(12) United States Patent
Dede et al.

(10) Patent No.: US 7,097,456 B1
(45) Date of Patent: Aug. 29, 2006

(54) AMALGAM SUBSTITUTE

(75) Inventors: Karsten Dede, Landsberg (DE); Oliver Frey, Gauting-Königswiesen (DE); Oswald Gasser, Seefeld (DE); Rainer Guggenberger, Herrsching (DE); Thomas Luchterhandt, Krailling (DE); Wolfgang Weinmann, Gilching (DE); Thomas Klettke, Schondorf (DE)

(73) Assignee: 3M ESPE AG, Seefeld (DE)

( * ) Notice: Subject to any disclaimer, the term of this patent is extended or adjusted under 35 U.S.C. 154(b) by 0 days.

(21) Appl. No.: 10/110,941

(22) PCT Filed: Oct. 20, 2000

(86) PCT No.: PCT/EP00/10342

§ 371 (c)(1),
(2), (4) Date: May 14, 2002

(87) PCT Pub. No.: WO01/28501

PCT Pub. Date: Apr. 26, 2001

(30) Foreign Application Priority Data

Oct. 22, 1999 (DE) ................. 199 51 063

(51) Int. Cl.
*A61C 5/00* (2006.01)
(52) U.S. Cl. .................. 433/226; 523/116
(58) Field of Classification Search ........ 433/226, 433/227, 228.1; 106/35; 523/116
See application file for complete search history.

(56) References Cited

U.S. PATENT DOCUMENTS

| 4,514,372 | A |   | 4/1985 | Devuyst et al. |
| 4,640,936 | A |   | 2/1987 | Janda et al. |
| 5,089,051 | A |   | 2/1992 | Eppinger et al. |
| 5,849,270 | A |   | 12/1998 | Podszun et al. |
| 5,962,550 | A | * | 10/1999 | Akahane et al. ............ 523/116 |
| 6,022,218 | A | * | 2/2000 | Alpert ........................ 433/215 |
| 6,084,004 | A |   | 7/2000 | Weinmann et al. |
| 6,172,131 | B1 |   | 1/2001 | Moszner et al. |
| 6,245,872 | B1 |   | 6/2001 | Frey et al. |
| 6,288,138 | B1 | * | 9/2001 | Yamamoto et al. ......... 523/118 |
| 6,350,344 | B1 |   | 2/2002 | Kinzelmann et al. |
| 6,407,148 | B1 | * | 6/2002 | Krejci et al. ................ 523/116 |

FOREIGN PATENT DOCUMENTS

| DE | 195 44 670 A1 | 6/1997 |
| DE | 197 43 564 A1 | 4/1998 |
| DE | 199 37 092 A1 | 2/2001 |
| DE | 195 44 670 C2 | 1/2003 |
| EP | 0 937 448 A2 | 8/1999 |
| WO | 99 25309 A | 5/1999 |
| WO | 99/34766 | 7/1999 |

OTHER PUBLICATIONS

Schafer, ZWR, 108.Jg., Nr. 5, S. 306-311. pp. 394-396, 1999.
Fouassier, *Photoinitiation, Photopolymerization and Photocuring Fundamentals and Applications*, Hanser/Gardner Publications, Inc., Cincinnati, U.S., Title page, Publication page, and Table of Contents (8 pgs total) (1995).

* cited by examiner

*Primary Examiner*—Melba N. Bumgarner
(74) *Attorney, Agent, or Firm*—Mueting, Raasch & Gebhardt, P.A.

(57) ABSTRACT

The invention relates to filling systems containing as component i) a sealing system which is capable of bonding to the tooth hard substance, as component ii) a filling material suitable for restorative dentistry, the filling system containing in addition a component iii) in component i) and/or component ii) which reduces the curing of the respective other component by disturbance of the curing mechanism only in the boundary layer between sealant and filling material such that the bonding between components i) and ii) is less than the bonding of component i) to the tooth hard substance.

13 Claims, No Drawings

AMALGAM SUBSTITUTE

This application is the national phase under 35 U.S.C. § 371 of PCT International Application No. PCT/EP00/10342 which has an International filing date of Oct. 20, 2000, which designated the United States of America.

FIELD OF THE INVENTION

The present invention relates to a dental filling system for filling therapy and its use as amalgam substitute.

DISCUSSION OF CONVENTIONAL ART

Amalgams—for example a mixture of a silver-tin alloy with liquid mercury—have been used for 150 years as standard filling material in restorative dentistry, being used in particular in the premolar and molar tooth area. With correct use, amalgam restorations are capable of guaranteeing the maintenance of tooth hard substance and also the vitality of the pulpa (so-called standard 1) and also the tooth form and function for years (so-called standard 2). Also decisive in the long-term success of amalgam fillings was the simple processing technique and the relatively low cost, as the average survival rate of an amalgam filling can be up to 10 years and more. Despite this, in recent years amalgam has increasingly lost its share of the market as the standard filling material. The main reason for this is the controversy about toxic and allergenic potential and also the damage to the environment and the absence of tooth colour. As materials were subsequently sought which could serve as substitute for amalgam, there were two different options available: on the one hand, the amalgam alternatives were developed and on the other hand, amalgam substitutes were sought.

The aim of the amalgam alternatives is to design the restoration such that it is indistinguishable from the surrounding tooth and also remains so during the whole application time (so-called standard 3).

As examples of this material group, there can be named in particular composites which are said to have not only the tooth colour but also a certain abrasion resistance and a perfect marginal adaptation. This is achieved by additionally using an adhesive system (also bond, bonding, bonding system, adhesive, sealant or sealing system) which must be used accurately in what is sometimes a complicated application.

In contrast to this, an amalgam substitute need only meet the previously named standard 2; in addition, the practical application—according to the amalgam—should take place simply and swiftly. This meant that it must be possible for example to work with steel moulds and wooden wedges, that a simple filling technique can be used, and in particular if a light curing is envisaged, that the latter must be possible directly from the occlusal surface. The layer-by-layer construction of the filling required with amalgam alternatives should be dispensed with and instead—again according to the amalgam—a so-called bulk filling be possible.

DE-A-196 03 577 describes an adhesive system which aims at a marginal-gap-free bond between the plastic material and tooth hard substance. The result of the excellent bond in such a system is that in the case of a failure of the adhesive system, the fracture occurs between tooth hard substance and the restorative material. This means however that in the case of a fracture on or in the tooth hard substance, there is no longer any protection against caries.

DE-A-195 44 670 describes an adhesive system which does not cure radically but in which a condensation reaction product is formed. In this manner, an oxygen-inhibition layer is avoided. With the use of this adhesive system—which again aims at the prevention of a marginal gap—according to the inventor, cohesive cracks in the dentine and enamel result. Consequently, this system is not capable of reliably preserving the tooth hard substance. The adhesive system therefore likewise belongs to a category which aims at an absolute bond between tooth hard substance and filling material without the cracking location being able to be predicted should cracking take place. Consequently, it can also occur between bond and tooth hard substance.

EP-A-0 423 430 describes a dentine adhesive system with a primer and a bond. Here also, a predominantly marginal-gap-free bond between tooth hard substance and restorative material is aimed at without it being able to be predicted where the marginal gap will occur in the case of a failure of the adhesive system.

EP-A-0 088 527 describes an enamel conditioner which is intended to produce a better bond between enamel and filling material than results from the etching process by phosphoric acid normally used.

DE-A-34 14 163 describes a dentine primer and a dentine bonding system which likewise aims at a predominantly marginal-gap-free bond between tooth hard substance and filling material.

In the state of the art, these adhesive systems are not used as pure sealing agent for the tooth hard substance. They are used exclusively as bonding material, the bond being produced between sealed tooth hard substance and the shrinking filling material. The adhesive systems of the state of the art uniformly aim at what is, in absolute terms, a greater bonding between the filling material and the tooth hard substance. The disadvantage of these systems is that it cannot be predicted where, in the case of a failure of the adhesive system, a crack will occur. In particular fractures in the boundary layer between adhesive system and the tooth hard substance or in the tooth hard substance are very damaging. A reliable protection thus cannot currently be guaranteed with use of adhesive and filling systems of the state of the art.

Studies show that with the filling systems known from the state of the art, for example composites in combination with their adhesive systems, which were developed as amalgam substitute, fillings are produced which—in particular in the case of occlusal stress—lead in a very short time to a marginal gap of over 60%, sometimes even up to 95% and more. This leads to marginal discolorations—which would still be acceptable within the framework of standard 2—and the development of secondary caries. With such marginal-gap phenomena, the risk of secondary caries development must be regarded as high to very high.

The materials which are proposed as amalgam substitute in the state of the art thus do not meet the previously named standard 1, i.e. the maintenance of the tooth hard substance over a prolonged period of time. Such materials should be used at most as temporary fillings.

The reason for the failure of the known amalgam substitute materials is that these materials normally display a volume shrinkage of 2.5 to 4.5% during curing. The resulting shrinkage stress on the bond and the tooth hard substance exceeds the strength of the bond or even the tooth hard substance. Under this shrinkage stress, unpredictable fractures therefore occur in the enamel or dentine or else also a break in the bond between tooth hard substance and adhesive system. Although an adhesive system is thus used, unprotected regions of the tooth hard substance result after the preparation, which are attributable to a cohesive fracture or a break between bond and tooth hard substance.

WO-99/25309 describes metal-free dental filling systems as amalgam substitute which seeks to overcome the previously named disadvantages of the current state of the art. It describes a dental filling system containing
a) a dental filling material and
b) an adhesive or a sealant for tooth hard substance,
c) the bond of the adhesive or the sealant to the tooth hard substance being stronger than to the filling material such that no destructive forces of the shrinking material are transmitted to the adhesive or the sealant.

In technical terms, the following solutions are proposed concerning same:
1. The use of an additional layer between filling material and sealant which prevents the transmission of destructive forces onto the sealant.
2. Between adhesive and filling material, or between intermediate layer and filling material, if present, there is no homo- or copolymerization.

This can be realized for example:
through a low radical content, by applying a powder or a coating, such as an organosilicone compound, which prevents a wetting of the two boundary surfaces,
through a different polarity between filling material and adhesive, which is likewise intended to prevent a wetting,
through a different hydrophobia or hydrophilia of filling material and sealant,
through a different curing system of filling material and sealant (for example a radically curing filling material and a cationically curing sealant).

In particular with the last method, DE-A-199 37 092 shows that with use of different polymerizing systems a very good bonding between adhesive and filling system is definitely achieved.

A major disadvantage of the technical solutions described is that new adhesive systems and/or filling systems which meet these requirements must be developed at high cost. None of the solutions shown in the named document contains the simple addition of substances to the sealing and/or filling system which disturb the initiator system of the respective other component.

SUMMARY OF THE INVENTION

The object of the present invention is to provide a simple dental filling system with which the bonding forces between sealant or adhesive system and filling material are weaker than between sealant or adhesive system and tooth hard substance, and which manages using customary dental materials and which requires no additional intermediate layer. Thus no new adhesive systems or filling materials need be developed.

This object is achieved by filling systems containing as component i) a sealing system which is capable of bonding to the tooth hard substance, as component ii) a filling material suitable for restorative dentistry, the filling system containing in addition a component iii) in component i) and/or component ii) which reduces the curing of the respective other component by disturbance of the curing mechanism only in the boundary layer between sealant and filling material such that the bonding between components i) and ii) is less than the bonding of component i) to the tooth hard substance.

The filling system according to the invention is thus such that component i) bonds to the tooth hard substance.

The terms "comprise" and "contain" indicate a non-conclusive enumeration of features.

The filling system preferably fulfils the equation a>0 and a>b>=0, a indicating the bonding value between tooth hard substance and sealing system and b the bonding value between sealing system and filling material.

The sealing system preferably bonds to the tooth hard substance such that after carrying out an adhesion test, more than 50%, preferably more than 80% of the surface of the tooth hard substance in the region examined is coated with the sealing system.

Depending on the nature of component iii), this can be a quantity of 0.01 to 99 wt.-%, preferably 0.25 to 95 wt.-% relative to the overall mass of component iii) and component in which component iii) is contained. All wt.-% data given hereafter are based on this.

The invention also relates to a kit which comprises the filling system according to the invention containing a sealing system and a filling system. Sealing system and filling system are as a rule packed separately from each other, preferably in the form of a disposable pack.

DETAILED DESCRIPTION OF THE INVENTION

In the following, the invention is described in more detail.

The bonding between components i) and ii) can be completely removed. It is clear for the dentist carrying out the treatment that he must then undertake the preparation of the cavity—analogously to the method customary with the amalgam—such that the retention of the filling material is mechanical (so-called undercut preparation).

Radical-forming initiators are described in detail in the literature (J.-P. Fouassier, Photoinitiation, Photopolymerization and Photocuring. Hanser Publishers, Munich, Vienna, N.Y., 1995). They can be substances activatable by UV- or visible light, such as benzoin alkyl ethers, benzil ketals, acylphosphinic oxides or aliphatic and aromatic 1,2-diketone compounds, for example camphorquinone, the catalyst activity being able to be accelerated by the addition of activators, such as tertiary amines or organic phosphites, in a manner known per se.

If for example an acylphosphinic oxide is used as radical initiator in the sealing system and a camphorquinone-amine system in the filling material, thus for example the catalyst of the filling material—i.e. the amine—can be inhibited by additions to the adhesive system—for example of acids. This takes place in such a way that, when the filling material is brought into contact with the adhesive, the acid from the adhesive penetrates the filling material, protonates the amine there and thus makes the latter unusable as a radical acceptor. Consequently, no radical initiation can take place in the boundary layer and no bonding between filling material and adhesive is possible.

When using acids as component iii), those are preferred which have a sufficient mobility of the protons, i.e. either a pKs value of <4.75 or, if their pKs value is greater than or equal to 4.75, are available in sufficient quantity. This means for first acids, for example, the use of strongly inorganic acids such as mineral acids, e.g. hydrochloric acid, sulphuric acid, phosphoric acid, super acids such as $HSbF_6$ or $HBF_4$, Lewis acids such as e.g. $BF_3$ adducts, acid metal salts such as $FeCl_3$, $AgNO_3$, or complex acids or precursors of acids such as acid chlorides or anhydrides. Similarly, compounds can be used which form strong acids with water or alcohols, such as saturated or unsaturated carboxylic acid halides.

Also suitable are unsaturated phosphoric acid and phosphonic acid derivatives as described in DE-A-198 06 572.8 and EP-A-0 909 761.

Also preferred are the hydrolysis-stable polymerizable acrylphosphonic acids of DE-A-197 46 708.

Particularly preferred is the use of the above acids in the adhesive system, where in a more preferred version the filling system contains an initiator system of camphorquinone and aliphatic amine.

It is true for second acids, such as more weakly acid acetic acid or carbonic acid derivatives, that they must be made available within the meaning of the compositions according to the invention in such a quantity that a pH value of less than 6 results on the sealing layer.

If for example compounds are used in the adhesive system which are themselves polymerizable and in addition are in a position to release protons, these compounds correspond to component iii) and their content can lie between 0.1 to 99 wt.-%, preferably between 3 to 90 wt.-% and particularly preferably between 5 to 75 wt.-%. The content of other acids can—depending on acid strength—lie between 0.1 to 80 wt.-%, preferably between 3 to 70 wt.-% and particularly preferably between 5 to 60 wt.-%.

Also suitable are acid fillers such as citric acid or acid-functionalized glasses or quartzes or those which make available the protons via other mechanisms, such as acid ion exchangers in combination with soluble salts. It is also conceivable to use these acid fillers likewise in the adhesive system, when their content should then lie between 3 to 60 wt.-%, preferably between 5 to 53 wt.-% and particularly preferably between 7 to 45 wt.-%. If they are used in the filling material, the content lies between 30 to 85 wt.-%, preferably between 40 to 82 wt.-% and particularly preferably between 50 to 80 wt.-%.

If the acids and/or acid fillers cannot be incorporated directly into the matrix of the adhesive or the filling material, it is also conceivable to subsequently apply to the adhesive a dissolved or suspended acid or an acid filler which then penetrates or diffuses into the adhesive. Preferred solvents are those such as water, alcohols, ketones such as acetone, methyl ethyl ketone, or also short-chained polymerizable compounds such as 2-hydroxymethacrylate or (2,3-epoxypropyl)-methacrylate.

In principle, the acid strengths of the acids used can be increased by additions of metal salts, the metal ions of which have a high affinity to the acid anion group.

A further possibility of the version according to the invention is for example the addition of cations which are capable of forming strong cation-amine complexes, such as copper, zinc, cobalt, silver or iron ions.

These compounds can be used in quantities of between 0.01 to 20 wt.-%, preferably between 1 to 10 wt.-% and particularly preferably between 1 to 5 wt.-%.

Another possibility of the version according to the invention is for example the addition of non-initiating amines—i.e. amines without abstractable α-protons such as triphenylamine or other HALS [hindered amine light stabilizers] to—in this case—the adhesive. As here also, the amine in the boundary layer diffuses into the filling material, there it takes over the place of the original initiator amine and thus prevents the polymerization in the boundary layer, which results in a "non-bonding". As examples of HALS there can be named triarylamines such as triphenylamine, 1,2,2,6,6-pentamethyl piperidines or compounds such as Tinuvin 292 or Tinuvin 123 (Ciba Speciality Chemicals, Switzerland).

These amines can be used in quantities of between 0.01 to 22 wt.-%, preferably between 1 to 15 wt.-% and particularly preferably between 1 to 12 wt.-%.

Similarly it is possible for example to inhibit the light-sensitive molecule—i.e. for example camphorquinone—according to the same mechanism by additions in the boundary layer. For these additions, there can be named for example:

Complexing agents for, for example, benzoin alkyl ethers, benzil ketals, acylphosphinic oxides or aliphatic and aromatic 1,2-diketone compounds (for example camphorquinone) such as Li salts or divalent chelating cations.

Compounds which react very fast with the previously named molecules such as primary amines, thiols or hydrazines.

These compounds are used quantatively between 0.01 to 22 wt.-%, preferably between 1 to 15 wt.-% and particularly preferably between 1 to 12 wt.-%.

Suitable initiator systems for triggering the radical polymerization via a redox mechanism are also for example the peroxide/amine, peroxide/barbituric acid derivatives or peroxide/acids systems.

If such systems are present in one of the two components i) or ii), it is possible for example to use additions in the other component which bind the amine irreversibly such as by acid chlorides or acid anhydrides. Naturally, the peroxide can also be inhibited in this way.

If one of the two components i) or ii) is cationically curing, additions which disturb the cationic initiation system are thus conceivable in the other component. Suitable as such additions are for example:

Basic compounds such as amines, basic salts, for example the oxides or hydroxides of the elements of the first to third main groups or sub-group, or basic fillers such as fine-grained glasses, and alcoholate salts. Also suitable are alkaline and alkaline earth halides and pseudohalides. Particularly preferred are Li salts, in particular Li salts of strong acids such as Li halides and Li tosylates.

With use of photoinitiator systems as described in DE-A-197 36 471 and in DE-A-197 43 564, additions for example such as the acids, acylphosphinic oxides or non-initiating electron donors described above are suitable.

These compounds can be used for example in quantities of between 0.01 to 30 wt.-%, preferably between 1 to 25 wt.-% and particularly preferably between 1 to 20 wt.-%.

If these compounds cannot themselves be directly incorporated into components i) or ii) due to for example solubilites or other effects, it is possible to dissolve or suspend them separately in a suitable solvent and only then to apply them to one of the respective components, the dissolved or suspended compounds then penetrating or diffusing into the respective components.

The application of components i) and ii) takes place in customary manner. In a preferred version, the tooth hard substance is not etched before the application of component i). If component iii) displays acid properties, a separate etching step is also not required, as the etching process takes place during the application.

In a further preferred version of the invention, component ii) is applied directly after component i).

EXAMPLES

In the following, the invention is described in more detail with the help of examples, which are to be considered as embodiments and in no way limiting.

Bonding Measurement on Bovine Teeth Through Adhesive Attachment of a Filling Material:

The adhesion bond was tested by an adhesion pull-off test on bovine teeth. Per test, 5 freshly extracted bovine teeth were ground down by means of sand paper until there was a sufficiently large exposed dentine surface. Wax platelets with a punched-out hole measuring 6 mm were glued onto each of these surfaces to obtain a standardized bonding surface. A quantity of the test mixtures sufficient for complete wetting of the test surface was then worked into the dentine surfaces with a microbrush for 20 seconds, blown briefly with compressed air and polymerized by means of a light polymerization device (Elipar Highlight™, ESPE) for 20 seconds. The filling material (Pertac II, ESPE, Seefeld) was then introduced into the holes of the wax platelets and fully polymerized by 40 seconds' exposure to light. The wax platelet was removed and the testpieces stored for 24 hours at 36° C. and 100% air humidity. The testpieces were then removed in a tensile test (Zwick Universal Test Machine).

The bonding values can be seen in Table 1.

To assess the residue of the sealant mixture, the sealant mixtures are reacted with 10 ppm Rhodamin B (Merck, Darmstadt) and the adhesion bond tested.

After carrying out the bonding test, a section 200 micrometers thick each of filling material and tooth hard substance is prepared perpendicular to the tooth or filling surface. The sections of tooth hard substance and filling material are observed by means of a fluorescence microscope (for example Axioplan, Zeiss) and the residue of the sealant mixture measured.

Preparation of the Reference Mixture:

To prepare 10 g of the reference mixture, the following constituents are intensively mixed together:
  3.000 g (30 wt.-%) 2-hydroxylethyl methacrylate;
  6.900 g (69 wt.-%) 10-methacryloyloxylethyl phosphate;
  0.100 g (1 wt.-%) bis(2,6-dichlorobenzoyl)-(4-butylphenoxy)phosphinic oxide;

Preparation of Sealant Mixture 1 According to the Invention:

To prepare 10 g of the sealant mixture 1, the following constituents are mixed together intensively:
  1.200 g (12 wt.-%) phosphoric acid;
  3.000 g (30 wt.-%) 2-hydroxyethyl methacrylate;
  5.700 g (57 wt.-%) 10-methacryloyloxyethyl phosphate;
  0.100 g (1 wt.-%) bis(2,6-dichlorobenzoyl)-(4-butylphenoxy)phosphinic oxide;

Preparation of the Sealant Mixture 2 According to the Invention:

To prepare 10 g of the sealant mixture 2, the following constituents are mixed together intensively:
  1.600 g (16 wt.-%) citric acid;
  2.600 g (26 wt.-%) 2-hydroxyethyl methacrylate;
  5.700 g (57 wt.-%) 10-methacryloyloxyethyl phosphate;
  0.100 g (1 wt.-%) bis(2,6-dichlorobenzoyl)-(4-butylphenoxy)phosphinic oxide;

Preparation of the Sealant Mixture 3 According to the Invention:

To prepare 10 g of the sealant mixture 3, the following constituents are mixed together intensively:
  0.800 g (8 wt.-%) triphenylamine;
  2.600 g (34 wt.-%) 2-hydroxyethyl methacrylate;
  5.700 g (57 wt.-%) 10-methacryloyloxyethyl phosphate;
  0.100 g (1 wt.-%) bis(2,6-dichlorobenzoyl)-(4-butylphenoxy)phosphinic oxide;

Preparation of the Sealant Mixture 4 According to the Invention:

To prepare 10 g of the sealant mixture 4, the following constituents are mixed together intensively:
  0.600 g (6 wt.-%) aqueous LiCl solution (15.67 wt.-%);
  3.000 g (30 wt.-%) 2-hydroxyethyl methacrylate;
  6.300 g (63 wt.-%) 10-methacryloyloxyethyl phosphate;
  0.100 g (1 wt.-%) bis(2,6-dichlorobenzoyl)-(4-butylphenoxy)phosphinic oxide;

The sealant mixture 4 was used in the bonding measurement tests in conjunction with a cationically curing filling material instead of Pertac II.

The preparation of the cationically curing filling material is described in the following:

In a three-finger kneader, the following constituents are kneaded into a homogeneous paste. There are used for 100 g paste:
  75.000 wt.-% (75.000 g) quartz (average grain size 0.9 μm, was silanized with 5 wt.-% glycidyloxypropyltrimethoxysilane);
  0.525 wt.-% (0.525 g) 4-methylphenyl-4-isopropylphenyl-iodoniumtetrakis-(penta-fluorophenyl)borate;
  0.223 wt.-% (0.223 g) camphorquinone (Merck, Darmstadt);
  0.001 wt.-% (0.001 g) ethyl-4-dimethylaminobenzoate (Merck, Darmstadt);
  0.001 wt.-% (0.001 g) 2-butoxyethyl-4-dimethylaminobenzoate;
  12.125 wt.-% (12.125 g) 3,4-epoxycyclohexyl-3,4-epoxycyclohexane carboxylate;
  12.125 wt.-% (12.125 g) 1,3,5,7-tetrakis-(2,1-ethanediyl-3,4-epoxycyclohexyl)-1,3,5,7-tetramethylcyclotetrasiloxane.

Preparation of the Sealant Mixture 5 According to the Invention:

The following constituents are mixed together corresponding to sealant mixtures 1 to 4 and both the bonding and the residue of the sealant layer examined:
  methacrylated phosphoric acid esters;
  water
  hydroxyethylene methacrylate;
  bis-GMA;
  acylphosphinic oxide;

The bonding was 3.5 MPa on dentine; the sealant layer remained predominantly on the tooth hard substance.

TABLE 1

Bonding of the sealant mixtures described in the examples:

| Sealant mixture | Filling material | Bonding [MPa]* |
|---|---|---|
| Reference mixture | Pertac II (ESPE Dental AG, Seefeld) | 2.3 |
| Sealant mixture 1 | Pertac II (ESPE Dental AG, Seefeld) | 0.0 |
| Sealant mixture 2 | Pertac II (ESPE Dental AG, Seefeld) | 0.0 |

TABLE 1-continued

Bonding of the sealant mixtures described in the examples:

| Sealant mixture | Filling material | Bonding [MPa]* |
|---|---|---|
| Sealant mixture 3 | Pertac II (ESPE Dental AG, Seefeld) | 0.0 |
| Sealant mixture 4 | Cationically curing | 0.0 |
| Sealant mixture 5 | Pertac II (ESPE Dental AG, Seefeld) | 3.5 |

*Average value of 5 measurements

With the sealant mixtures 1 to 4, no bonding of the filling material to the bond took place. The bond remained largely undamaged on the tooth hard substance after removal of the filling material. With the reference mixture on the other hand, the sealant mixture remained predominantly on the filling material.

As the sealant mixtures according to the invention remain predominantly on the tooth hard substance, it is proved that the bonding of the sealant mixture to the tooth hard substance is greater than to the respective filling material.

What is claimed is:

1. A filling system comprising:
   (i) a curable sealant component which is capable of bonding to a tooth hard substance,
   (ii) a curable filling material component suitable for restorative dentistry, and
   (iii) a curing reduction component selected from the group consisting of:
   acids having a pKa value of less than 4.75, Lewis acids, acid metal salts, acid precursors, compounds which form strong acids with water, compounds which form strong acids with alcohols;
   a cation which forms cation-amine complexes;
   a non-initiating amine;
   a lithium salt;
   a divalent chelating cation compound;
   oxides of elements of the first to third main groups and subgroups of the Periodic Table of Elements, hydroxides of elements of the first to third main groups and subgroups of the Periodic Table of Elements, alkaline halides, alkaline earth halides and pseudohalides;
   wherein said component (iii) is incorporated in the said component (i) and component (ii), and
   wherein, upon curing of the sealant and filling material components, component (iii) reduces curing only in a boundary layer between sealant component and filling material component such that the bonding between the cured sealant component and the cured filling material component is less than the bonding of the cured sealant component to the tooth hard substance.

2. The filling system according to claim 1, wherein one of the sealant component (i) or the filling material component (ii) comprises as a curing initiation system a camphorquinone-amine system, and the other of these components comprises as a curing initiation system an acylphosphine system.

3. The filling system according to claim 1, wherein the filling material component (ii) is cationic, and the curing reduction component (iii) is incorporated in the sealant component (i) which cures radically.

4. The filling system according to claim 1, wherein the curing reduction component (iii) is an acid having a pKa value of less than 4.75 selected from the group consisting of hydrochloric acid, sulphuric acid, phosphoric acid, $HSbF_6$, $HBF_4$, $BF_3$ adducts, $FeCl_3$, and $AgNO_3$.

5. A filling system according to claim 1, wherein the curing reduction component (iii) is with a cation selected from the group consisting of copper, zinc, cobalt, silver and iron cations.

6. A filling system according to claim 1, wherein the curing reduction component (iii) is a non-initiating amine selected from the group consisting of triphenylamine and hindered amine light stabilizers.

7. A filling system according to claim 1, wherein the curing reduction component (iii) is a non-initiating amine selected from the group consisting of triphenylamine and 1,2,2,6,6-pentamethyl piperidines.

8. A filling system according to claim 1, wherein the curing reduction component (iii) is a lithium salt selected from the group consisting of lithium halides and lithium tosylates.

9. A kit comprising a filling system comprising
   (i) a curable sealant which is capable of bonding to the tooth hard substance,
   (ii) a curable filling material suitable for restorative dentistry, and
   (iii) a curing reduction component selected from the group consisting of:
   acids having a pKa value of less than 4.75, Lewis acids, acid metal salts, acid precursors, compounds which form strong acids with water, compounds which form strong acids with alcohols;
   a cation which forms cation-amine complexes;
   a non-initiating amine;
   a lithium salt;
   a divalent chelating cation compound;
   oxides of elements of the first to third main groups and subgroups of the Periodic Table of Elements, hydroxides of elements of the first to third main groups and subgroups of the Periodic Table of Elements, alkaline halides, alkaline earth halides and pseudohalides;
   wherein said curing reduction component (iii) is incorporated in the sealant and/or the filling material, and
   reduces curing only in a boundary layer between the sealant and the filling material such that the bonding between the cured sealant and the cured filling material is less than the bonding of the cured sealant to the tooth hard substance,
   wherein the sealant and the filling material are packed separately from each other.

10. The kit according to claim 9, wherein the curing reduction component (iii) is packed separately from the sealant component (i) and the filling material component (ii).

11. A method for filling a tooth, comprising the steps of:
    (a) applying a sealant to the tooth hard substance,
    (b) optionally exposing the sealant to light,
    (c) applying a filling material,
    (d) exposing the filling material to light, and
    (e) applying to the sealant before step (c), or incorporating into the sealant or filling material before application thereof, a curing reduction component selected from the group consisting of:
    acids having a pKa value of less than 4.75, Lewis acids, acid metal salts, acid precursors, compounds which form strong acids with water, compounds which form strong acids with alcohols;

a cation which forms cation-amine complexes;
a non-initiating amine;
a lithium salt;
a divalent chelating cation compound;
oxides of elements of the first to third main groups and subgroups of the Periodic Table of Elements, hydroxides of elements of the first to third main groups and subgroups of the Periodic Table of Elements, alkaline halides, alkaline earth halides and pseudohalides;
wherein said curing reduction component reduces curing in a boundary layer between the sealant and the filling material, such that bonding between the cured sealant and the cured filling material is less than between the cured sealant and tooth hard substance when neither the sealant nor the filling material contains said curing reduction component.

12. The method according to claim 11, wherein the tooth hard substance is not etched before step (a).

13. The method according to claim 11, wherein the filling material is applied directly after the application of the sealant.

* * * * *

UNITED STATES PATENT AND TRADEMARK OFFICE
CERTIFICATE OF CORRECTION

PATENT NO. : 7,097,456 B1
APPLICATION NO. : 10/110941
DATED : August 29, 2006
INVENTOR(S) : Dede et al.

Page 1 of 1

It is certified that error appears in the above-identified patent and that said Letters Patent is hereby corrected as shown below:

In column 4, line 60, delete "<4.75" and insert -- ≤4.75 --.

Signed and Sealed this

Eleventh Day of December, 2007

JON W. DUDAS
*Director of the United States Patent and Trademark Office*